United States Patent [19]

Kane et al.

[11] Patent Number: 5,096,671
[45] Date of Patent: Mar. 17, 1992

[54] FIBER OPTIC CHEMICAL SENSORS INCORPORATING ELECTROSTATIC COUPLING

[75] Inventors: James A. Kane; Leonard Pinchuk, both of Miami, Fla.

[73] Assignee: Cordis Corporation, Miami Lakes, Fla.

[21] Appl. No.: 324,239

[22] Filed: Mar. 15, 1989

[51] Int. Cl.[5] .................. G01N 21/64; B05D 5/06
[52] U.S. Cl. .................. 422/82.07; 128/634; 356/39; 356/412; 385/12; 422/82.06; 422/82.11; 427/163; 436/68; 436/166
[58] Field of Search ........... 422/82.06, 82.07, 82.11; 436/68; 350/96.29; 356/39, 412; 128/634; 385/12; 427/163, 164, 165, 169, 443.2; 436/166

[56] References Cited

U.S. PATENT DOCUMENTS 4,999,306 4/1991 Yafuso et al. .............. 422/82.07 X

Primary Examiner—Jill A. Johnston
Attorney, Agent, or Firm—Lockwood, Alex, Fitzgibbon & Cummings

[57] ABSTRACT

Fiber optic chemical sensors and materials suitable for use in making same are provided. A charged hydrogel matrix membrane is suitable for affixing to the distal end portion and the like of an optical fiber waveguide, which charged hydrogel matrix has dispersed therewithin an oppositely charged ion exchange resin powder, which ion exchange powder has a colorimetric indicator component electrostatically coupled thereto, which colorimetric indicator component has the same charge as the charged hydrogel.

19 Claims, 1 Drawing Sheet

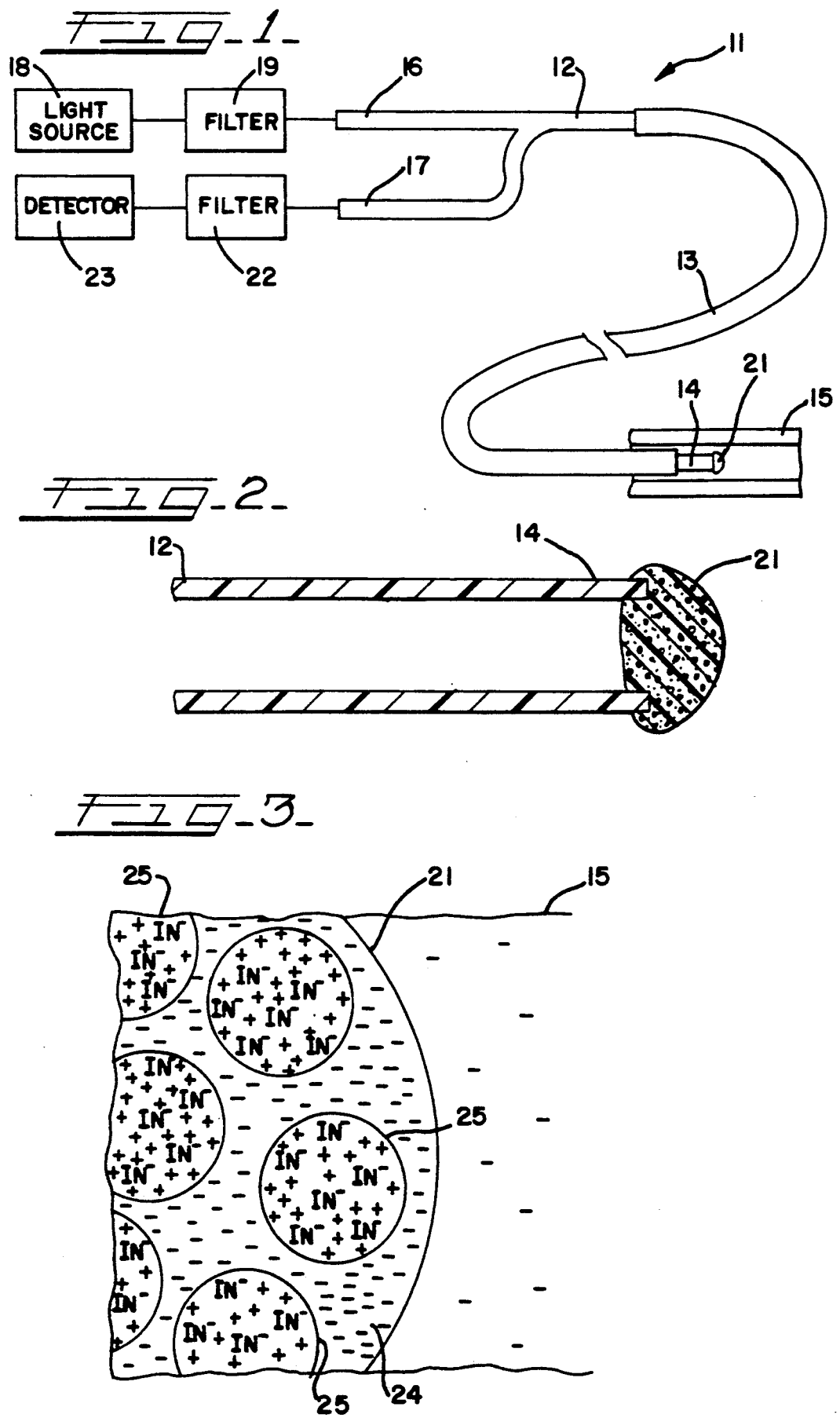

FIBER OPTIC CHEMICAL SENSORS INCORPORATING ELECTROSTATIC COUPLING

BACKGROUND AND DESCRIPTION OF THE INVENTION

The present invention generally relates to chemical sensors for monitoring, detecting and/or measuring parameters at locations remote from detection instrumentation. More particularly, the invention relates to chemical sensor components that are positioned at a remote or distal portion of an optical fiber waveguide, which chemical sensor components incorporate a charged indicator component electrostatically coupled to oppositely charged ion exchange resin material dispersed within a charged hydrogel matrix membrane.

Chemical sensors secured to the distal end of optical fibers are generally known to be useful for a wide variety of purposes, especially in the areas of medicine, scientific research, industrial applications and other situations where it may be desired to detect and/or measure the concentration of a parameter at a remote location without requiring electrical communication with the remote location. Descriptive materials which describe the structure, properties, functions and operational details of fiber optic chemical sensors include U.S. Pat. Nos. 4,577,109 and 4,785,814, as well as Sietz, "Chemical Sensors Based on Fiber Optics", *Analytical Chemistry*, Vol. 56, No. 1, January, 1984, each of which is incorporated by reference hereinto.

Publications such as these generally illustrate that it is known to incorporate a chemical sensor into a fiber optic waveguide in a manner such that the chemical sensor will interact with the analyte. This interaction results in a change in optical properties, typically a change in color or color intensity, which is transmitted through the fiber optic waveguide and to a suitable detection device. In these types of systems, it is possible to detect particularly minute changes in the parameter being monitored in order to thereby provide especially sensitive remote monitoring capabilities.

Chemical sensor compositions that are incorporated at the distal end of these types of fiber optic sensors are often configured as membranes that are secured at the distal tip end of the waveguide device or optrode. Specific examples of membranes for optrodes are found in U.S. Pat. No. 4,272,485, which proposes a variety of membrane mobile carrier substances for transporting particles within the membrane. In this patent, a carrier is described which may be either charged or uncharged that takes up particles in the solution being monitored and transports them through the membrane and into the optrode. The carrier is characterized as being mobile within the membrane and as transporting the particles through the membrane. Highly selective indicators, as well as a broadened range of measurement applicability, are said to be achieved by this transport carrier approach.

Optrodes having chemical sensors such as those discussed in these publications are useful in monitoring or measuring pH, oxygen concentrations, carbon dioxide concentrations and the like. Cation concentrations can also be detected, such as potassium, sodium, calcium ions, as well as metal ions. Often, these types of devices are used in medical applications for in vivo monitoring of biological fluids. Other areas in which fiber optic chemical sensors may be useful include the monitoring of chemical conditions during industrial processes, such as taking industrial biological measurements. An example of the specific industrial type of application includes the use of optical fibers for measuring conditions within submerged wells and the like.

It has been determined that, by proceeding in accordance with the present invention, it is possible to utilize opposite charges of interacting components in order to substantially irreversibly bind the color indicator within a matrix that can function as a membrane which adheres to a fiber optic in order to provide an optrode arrangement that will be useful in monitoring various parameters of the types discussed herein. Ion exchange resin powders having the indicator material electrostatically coupled thereto are dispersed within a charged hydrogel membrane material carrying an overall charge that is opposite to the charge presented by the ion exchange resin powder. The present invention preferably includes the use of a water-insoluble cationic ion exchange resin bound to an anionic color indicator, which resin and indicator combination is dispersed in an anionic hydrogel matrix that adheres to a fiber optic waveguide in order to thereby provide an optrode assembly. When desired, the various materials can be selected in order to provide a fiber optic waveguide and optrode assembly that is biocompatible.

It is a general object of the present invention to provide an improved fiber optic chemical sensor.

Another object of the present invention is to provide an improved fiber optic chemical sensor that utilizes ion exchange resin technology whereby opposite charges can be advantageously utilized to form a membrane or matrix that is especially durable while still presenting an optrode that is colorimetrically responsive to desired parameters or components.

Another object of this invention is to provide an improved fiber optic chemical sensor that is biocompatible and very non-thrombogenic.

Another object of the present invention is to provide an improved fiber optic chemical sensor which simplifies retention of the dye component therewithin by ionically retarding leaching thereof.

Another object of this invention is to provide an improved fiber optic chemical sensor that presents an anionic surface which reduces the likelihood that components within the bloodstream or the like would interfere with the fluorescent signal developed by the sensor.

These and other objects, features and advantages of this invention will be clearly understood through a consideration of the following detailed description.

BRIEF DESCRIPTION OF THE DRAWINGS

In the course of this description, reference will be made to the attached drawings, wherein:

FIG. 1 is a generally schematic view, partially broken away, of an optical probe assembly including a fiber optic chemical sensor device in accordance with the present invention;

FIG. 2 is an enlarged, cross-sectional view of the fiber optic chemical sensor illustrated in FIG. 1; and FIG. 3 is an even further enlarged and generally schematic illustration of a portion of a preferred fiber optic chemical sensor illustrated in sensing communication with a bloodstream or the like.

DESCRIPTION OF THE PARTICULAR EMBODIMENTS

An optical probe assembly is generally designated as 11 in FIG. 1. Assembly 11 includes an optical fiber 12 slidably positioned through the lumen of a catheter 13 in order to facilitate positioning of distal end 14 of the optical fiber 12 within a blood vessel 15 of a patient. This illustration is of a usual positioning of an optical probe assembly for monitoring blood parameters of a patient. Other optical probe assemblies could be utilized as desired.

In the illustrated optical probe assembly 11, the optical fiber 12 is bifurcated at its proximal portion so as to define an input pathway 16 and an output pathway 17. Input pathway 16 receives light from a light source 18, typically through a filter 19. During use, this filtered light supply is transmitted through the optical fiber 12 and to a chemical sensor 21, which in this illustration is located at the distal tip end of the optical fiber 12. Chemical sensor 21 responds to ions or other parameters within the blood vessel 15 or the like which are to be monitored. These responses are colorimetric in nature and are transmitted through the optical fiber 12 and, by suitable means typically including a filter 22, are received by a detector 23 for converting the colorimetric output into data needed to determine the concentration or the like of the ion or other parameter that is being monitored or measured. When used herein, the term colorimetric refers to color changes as well as to changes in intensity of fluorescence.

As can be perhaps best seen in FIG. 2, the chemical sensor 21 is adhered to the distal end 14 of the optical fiber 12. Any suitable securement arrangement can be used. The one illustrated is a relatively simple attachment of the chemical sensor 21 to the material of the optical fiber 12. This relatively simple assembly procedure is facilitated somewhat by the physical and chemical properties of the chemical sensor 21, including its durability and ability to be used without experiencing any significant swelling.

With more particular reference to the chemical sensor 21, important features of a preferred embodiment thereof are generally schematically illustrated in FIG. 3. Included is an anionic hydrogel matrix membrane 24 which provides the basic structure of the chemical sensor 21. This anionic matrix membrane is adhered to the inside end, outside end and distal edge of the distal end portion 14 of the optical fiber 12. Cationic ion exchange resin beads or powder components 25 are dispersed within and throughout the anionic matrix member 24. An anionic colorimetric indicator component, designated by IN⁻ in FIG. 3, is electrostatically coupled to the cationic ion exchange resin beads or powder components 25.

By these structures, a fiber optic sensor or optrode for the measurement of parameters of fluids, such as physiological parameters including pH, carbon dioxide concentration and oxygen concentration within the bloodstream of a patient, are provided. The water insoluble cationic ion exchange resin 25 is substantially irreversibly bound to the anionic dye or the like, and the cationic resin 25 containing the dye is dispersed in the anionic matrix 24 which is capable of adhering to the optical fiber 12, and the anionic matrix 24 also imparts a biocompatible surface to the optrode. The cationic dye changes in absorbence or fluorescence depending upon the concentration of the species or parameter to be measured or monitored.

Concerning the charged hydrogel matrix membrane 24, this material must be a hydrophilic charged material having a charge opposite of the resin 25. Matrix membrane 24 should be soluble within a solvent within which the cationic ion exchange resin is dispersible. In addition, it should be bondable to an optical fiber, typically by solvent bonding techniques. It should be biocompatible and exhibit adequate durability within the environment of its intended use. The charged hydrogel matrix membrane 24 should exhibit a refractive index so that the indicator will be visible via the optical fiber. Furthermore, the charged hydrogel matrix membrane should not swell to such an extent that it would shear from the optical fiber when in use.

A class of materials that may be suitable as an anionic hydrogel matrix membrane are polyurethane urea materials which include anionic moieties. When such materials are to be used in vivo, care should be taken that components of the membrane material, such as the anionic moieties thereof, do not form undesirable components, such as acids that would be unsuitable for use within the body. Cationic matrix membrane materials include copolymers of hydroxyalkyl methacrylates and tertiary amino alkyl methacrylates, for example tert-butyl aminoethyl methacrylate and hydroxyethyl methacrylate. An example of an anionic matrix membrane material is a copolymer of sulfoethyl methacrylate sodium salt and hydroxyethyl methacrylate. These copolymers can be modified to make them photogelling by post-polymerization grafting with acryloyl chloride or the like.

An exemplary polyurethane urea having an anionic moiety is the sodium salt of sulfonated aromatic polyurethane, which can be represented by the following formula:

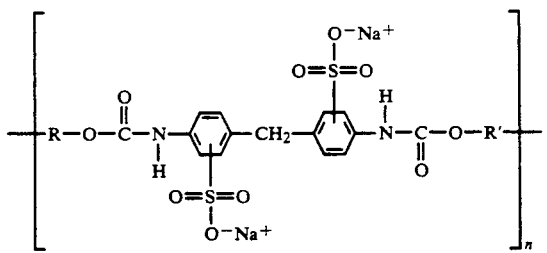

where R and R' are generally alkyl groups and R may be the same as R'; and n is an integer greater than 1. The anionic sulfonated polymer is believed to contain one sulfur trioxide moiety per aromatic group. Preferably, the sulfonation step is followed by treatment with a mild base, such as 2% solution of sodium carbonate, to neutralize residual acid and to ionize the resultant sulfur trioxide moiety.

It is typically preferred to use an adduct made from a primary alcohol and sulfur trioxide for such sulfonation. The adduct utilized is preferably comprised of the Lewis complex of sulfur trioxide and a primary alcohol such as methanol, ethanol, 1-propanol, 1-butanol, or the like. It is generally known that the sulfur atom on the sulfur trioxide moiety is an electrophile, or a Lewis acid, and will combine with a nucleophile, or Lewis base, to form coordination compounds or adducts. In the case of an adduct of sulfur trioxide and ethanol, it is believed that the reaction can be depicted as follows:

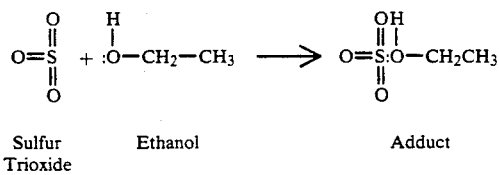

Upon sulfonation of an organic compound, the sulfur trioxide is believed to be released from the alcohol so that it may react with the aromatic group of the polymer to form the salt of the new acid. Further treatment with a mild base, such as sodium carbonate, yields the sodium salt of the sulfonated polymer. In the case of aromatic polyurethane, the reaction can be depicted as follows:

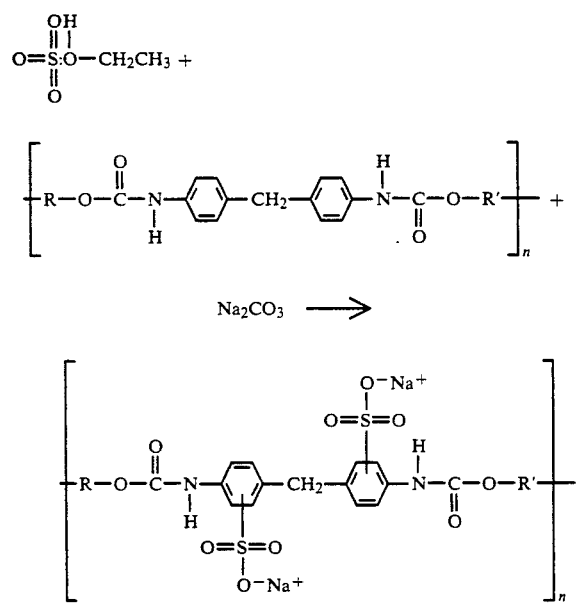

Other adducts for sulfonating aromatics in solution are known, such as sulfur trioxide in the tetrahydrofuran, ethylene triamine, triethyl phosphate, dimethyl formamide, and dimethyl acetamide.

This sulfonation of aromatic polymers may be accomplished by submerging the aromatic polymer in fuming sulfuric acid which has been previously cooled to 0°–10° C. in an ice bath or the like. The polymer should remain submerged in the acid for about 5 to 10 seconds, depending on the material used. In the case of aromatic polyurethanes, for example, sulfonation is very rapid and is evidenced by a dramatic color change to a bright orange-red. The polymer may then be removed from the acid and, if desired, be quenched by immersion in distilled water for 30 seconds, more or less. The polymer is then soaked in a weak base, such as a 2% solution of sodium carbonate, for approximately 1 minute. Extractables may then be leached out by soaking the sulfonated polymer in distilled water for a few hours.

Alternate methods of sulfonating the aromatic rings include sulfonating the aromatic diisocyanate prior to polymerization of the polyurethane and sulfonating the polymer in solution after polymerization. The former can be performed using conventional wet chemistry techniques such as sulfonating the aromatic rings directly with adducts of sulfur trioxide and dimethylacetamide. The sulfonated aromatic diisocyanate can then be solvent extracted with an appropriate solvent then polymerized to a polyurethane in the conventional manner. The polyurethane can be sulfonated in solution after polymerization if performed in a mutually compatible solvent for both the polyurethane and the sulfur trioxide adduct. Possible solvents include dimethylsulfoxide, dimethylformamide and the like.

Additionally, this sulfonation may be accomplished by exposing the aromatic polymer directly to sulfur trioxide vapor or by using concentrated sulfuric acid. Where concentrated sulfuric acid is used, water contamination must be kept below the 20% level in order to avoid dissolution of the aromatic polyurethane. When sulfur trioxide vapors or concentrated sulfuric acid are used to sulfonate, it may be necessary to slightly increase the time in which the polymers are exposed to either the concentrated acid or the sulfate vapor so that an effective exposure time may exceed the time required when fuming sulfuric acid is utilized.

Generally, the charged hydrogel matrix polymer membrane materials are put into solution in practicing the present invention. Suitable solvents for perfluorinated ion exchange powders include lower aliphatic alcohols and mixtures thereof, as well as acetone, and combinations of alcohols and acetone. Typical urethane solvents can be used for polyurethane urea membrane materials, including dimethyl acetamide, tetrahydrofuran, methylene chloride, and the like. The solvents should possess sufficient polarity in order to effect solvent bonding thereof to optical fibers including those made of materials such as polymethyl methacrylate, polystyrene and the like. Typically, the charged hydrogel matrix membrane can be affixed to the optical fiber by dipping and drying techniques.

The oppositely charged ion exchange resin beads or power components that are dispersed within the charged hydrogel matrix membrane are charged ion exchange resins that are water insoluble and that substantially irreversibly bind a charged material thereto. More specifically, they irreversibly bind the charged indicator component thereto. This property of the ion exchange resin is illustrated in FIG. 3 wherein cationic ion exchange resin beads or powder components 25 exhibit positively charged sites to which an anionic indicator, depicted as IN⁻, is bound. Typically, such ion exchange resins are of the type that are commercially available and known to be useful for separating species by their geometry, polarity and ionicity. Examples of resins in this regard include tertiary amine functionalized cellulose particles, quaternary ammonium styrene resins, alumina and silica. Generally speaking, such resins are beads that are insoluble, but water wettable. They can also exhibit a variety of cross-linked densities, with the degree of cross-linking affecting the binding ability of certain species. Usually, the greater the cross-linking, the more difficult it is to diffuse the charged indicator component into the charged hydrogel matrix and, conversely, the more difficult it is to remove the charged indicator component once it is in the matrix. In order to generally balance these attributes, medium levels of cross-linking usually are the most suitable.

Typical commercially available charged ion exchange resin materials are supplied as small beads with diameters in the range of 0.1 to 2 mm. In practicing the present invention, it is preferred to grind these beads to micron sized particles, for example by shearing them in a blender at high speed for a few minutes in order to form a charged ion exchange resin powder. It is usually desirable to sieve this powder to contain particles that are substantially all of a diameter less than about 50 microns.

With more particular reference to the charged indicator component according to the present invention, same includes a molecule that undergoes a change in color or color intensity as a function of the species to be measured, such as pH, oxygen concentration, carbon dioxide concentration and the like. In some instances, such as carbon dioxide concentration, the indicator may actually indirectly measure the particular species by directly measuring another species (such as pH) which is then recognized through suitable means as a concentration of the species being monitored. Anionic indicators, in addition to containing a negative charge (so that the cationic resin will exchange anions when combined therewith), typically include aromatic rings. Examples of anionic indicator dye components include sodium salts of pH indicator dyes such as phenol red or bromothymol blue and fluorescent pH indicators such as 8-hydroxypyrene-1,3,6-trisulfonic acid. Fluorescent dyes that are capable of being quenched in the presence of oxygen and that can be used as cationic sensors for the oxygen concentration in blood include ruthenium complexes such as tris(4,7-diphenyl 1,10-phenathroline) ruthenium II chloride.

In forming the fiber optic chemical sensors according to this invention, this charged dye indicator component is placed in solution with the ion exchange resin powder. When the indicator is anionic and the resin cationic, the positive or cationic nature of the ion exchange resin powder provides the affinity necessary to attract the negative or anionic dye into the matrix of the anionic exchange resin powder. The procedure of adsorbing such an anionic indicator component into the resin can be facilitated by dissolving the indicator in distilled water and adding the cationic resin to this solution. Once the indicator component is in the ion exchange resin, which can be detected by a clearing up of the solution, the resin is rinsed repeatedly in water until no residual indicator component is observed to leach from the resin. By this procedure, the charged indicator component remains trapped within the swollen resin in an acidic solution by virtue of the ionic attraction of the charge indicator component and the oppositely charged resin matrix, by van der Walls forces, and by hydrophobic bonding.

Next, the ground ion exchange resin powder containing the electrostatically attached indicator component is dispersed into the solution containing the charged hydrogel matrix membrane material. The fiber optic, for example a polymethyl methacrylate core fiber optic that is cleaved and/or polished to an optical finish, is then dipped into this solution, withdrawn and dried.

An optrode thus prepared operates when light of an appropriate wavelength is directed into the fiber, usually by means of a light bifurcating device and focusing-/filtering optics of the type generally shown in FIG. 1, as necessary. The light is supplied, for example, by light emitting diodes, incandescent bulbs, lasers, and the like. The light source must exhibit a measurable spectral component which overlaps the absorbtion band of the indicator dye. For example, for a pH indicator such as phenol red, that absorption band is centered around 558 nm. Light from the source is carried by the fiber to the optrode where it interacts with the indicator on the resin to reflect a signal proportional to the concentration of the parameter being measured. This optical signal is carried back up the fiber, bifurcated, focused and detected. Silicon photodiodes and photomultipliers are typical photo detectors. When filtering devices are used, they can be monochromators, dichroic filters, bandpass and narrow band dielectric stacks.

Light being carried by the fiber may interact with the sensing elements using either of two geometries—side of fiber or end of fiber. In a side-of-fiber approach, the light interacts with the sensor element through an evanescent wave produced at the core modified cladding interface. This evanescent wave is the result of the interference of the incident and reflected light at the interface of the cladding and the sensing polymer. Because the wave penetrates a portion of the sensing polymer, it may be attenuated by, or produce fluorescence in, a pH indicating dye retained by the ion exchange resin. In this type of arrangement, the surface length of the side optrode should be greater than the surface length at the tip of the fiber. When an end-of-fiber approach is followed, the light from the fiber impinges on the particles in the polymer directly. A small portion of incident light is scattered and is caused to return into the fiber attenuated by the characteristic absorption of the acid-base form of the dye.

The fiber optic chemical sensors according to the present invention are very non-thrombogenic, are durable, and do not swell excessively. By the combination of the charged hydrogel membrane and the like-charged indicator component, there is a charge repulsion condition which enhances the retention of the indicator component within the resin. Without such a charge repulsion (for example if the matrix or membrane were uncharged or neutral, the indicator component would leach slowly from the membrane).

Additionally, when monitoring blood that is treated with certain components, for example an anesthetic such as sodium pentabarbital, the fiber optic chemical sensors according to present invention are less likely to experience false fluorescent signals than might be experienced by other chemical sensors that do not present a charged (such as an anionic) surface. Most interfering substances such as this type of sodium barbiturate anesthetic are anionic in the bloodstream. A fiber optic chemical sensor such as illustrated in FIG. 3 repels same in order to reduce interference thereof with the detection accomplished by the chemical sensor in view of the fact that these otherwise interfering substances are distanced from the chemical sensor by the operation of such charge repulsion attributes.

Another advantage of fiber optic chemical sensors according to the present invention is as follows. When an anionic hydrogel matrix is used, the anionic nature of the matrix membrane is particularly suitable for indicators that absorb blue-green light, and these types of chemical sensors readily immobilize red cationic dyes on their surface in order to provide a red-coated chemical sensor. Such a red coloration assists in attenuating the excitation and to maintain the initial calibration of the chemical sensor. The red coloration generally screens out undesirable effects of so-called double pumping due to the presence of red blood cells during in vivo uses.

The following examples are illustrative of fiber optic chemical sensors as discussed herein.

EXAMPLE 1

A Fluorescent pH Fiber Optic Sensor

Preparation of the Indicator Dye and Ion Exchange Resin

A cross-linked anion exchanging resin, such as the tertiary amine functionalized cellulose DEAE-SERVACEL from Serva Chemicals, is ground in an amalgamator to a particle size of 50 microns or less. These particles are mixed for 1 hour in aqueous solution with an anionic fluorescent pH indicator such as the sodium salt of the fluorescent pH indicator 8-hydroxypyrene 1,3,6-trisulfonic acid. The solution is then filtered through a number 2 Whatman filter and the stained moist particles collected.

Preparation of a Photogelling Anionic Matrix Polymer

To a 100 ml. round bottom flask fitted with an additional funnel, magnetic stirring bar, nitrogen purge and vent, is added 50 ml. of water, 94 mg. ammonium persulfate and 70 mg. sodium metabisulfite. The solution is stirred, heated to 60° C. and rigorously purged of oxygen by a stream of dry nitrogen. To the addition funnel fitted on the round bottom flask is added a solution of 2.4 grams of the sodium salt of sulfoethyl methacrylate, 7.2 ml. hydroxyethyl methacrylate and 5.4 ml. water. The contents of the addition funnel are also purged of oxygen with a nitrogen stream. The contents of the addition funnel are then added to the flask solution while maintaining a stream of nitrogen into the flask. The nitrogen purge and 60° C. heating of the solution is maintained for a period of 1 hour. Following the hour period, the solution is allowed to cool to room temperature and the purge discontinued.

The contents of the flask are then diluted to a volume of 1 liter with distilled water. The polymer formed in the reaction is precipitated from this solution by addition of 150 grams of sodium chloride. The solid, white polymer precipitate is collected and dried in a vacuum oven at 60° C. under reduced pressure.

The dried polymer is redissolved in 50 ml. of dry dimethyl formamide and the solution cooled in an ice bath of 0° C. To this solution is then added, with stirring, a solution of 100 microliters of acryloyl chloride in 10 ml. of dimethyl formamide. The grafting reaction is stirred at 0° C. for 2 hours.

The acryloyl chloride grafted copolymer in dimethyl formamide is then diluted to 1 liter with cold distilled water. To the cold aqueous polymer solution is added 150 grams of sodium chloride, and the polymer is precipitated. The precipitate is dried in a vacuum oven at 60° C. under reduced pressure, then redissolved in distilled water at a concentration of 50 weight percent.

Preparation of the Optrode 0.25 gram of the stained particles are dispersed in 10 ml. of the photogelling polymer derivative solution described above. To this solution is added 10 microliters of the water soluble photoinitiator 2-hydroxy-2-methylphenylpropan-1-one. A polymethyl methacrylate cored optical fiber is cleaved and/or polished to an optical grade finish. This fiber end is then dipped into the ion exchange resin/dye/polymer derivative solution and withdrawn. The fiber retains a small volume of the resin/dye/polymer solution. This small volume is purged of oxygen by placing the fiber tip in a stream of dry nitrogen for five minutes. The optrode is then formed by irradiating the tip with a high intensity blue light from a source such as an arc lamp. Alternatively, the light may be introduced to the end of the fiber by pumping with the arc lamp into the fiber end that is not dipped into the resin/dye/polymer. The formed optrode is then cleaned by soaking in distilled water for 24 hours.

How the Sensor Operates

Light of an appropriate wavelength is directed into the fiber by means of a light bifurcating device and focusing/filtering optics, if necessary. Examples of light sources include light emitting diodes, incandescent bulbs, and lasers. A requirement of the light source is sufficient spectral overlap of its emission with the absorbance spectrum of the indicator dye. For the pH indicator given in this Example, 8-hydroxypyrene 1,3,6-trisulfonic acid, that absorbance band in the base form of the dye is centered around 470 nm., which is easily pumped by a blue LED (Siemens LDB 5410).

Light of the source is carried by the fiber to the optrode where it interacts with the pH indicator on the ion exchange resin to produce a fluorescent signal centered at 525 nm. of an intensity proportional to the pH of the medium into which the optrode has been placed. This fluorescence is then carried back up the fiber, bifurcated, filtered to remove any scattered excitation light, focused and detected. Examples of filtering devices include monochromators, dichroic filters, bandpass and narrowband dielectric stacks. Examples of photo detectors include silicon photodiodes and photomultipliers.

EXAMPLE 2

A Fiber Optic Oxygen Sensor

Preparation of the Indicator Dye and Ion Exchange Resin

A cross-linked polystyrene ion exchange resin containing sulfonate groups is ground in an amalgamator to a particle size of 50 microns or less. These particles are dried by repeated washings with anhydrous methanol. One gram of the dried particles is dispersed in 10 ml. of anhydrous methanol. To the particles/alcohol is added 1 ml. of a $10^{-5}$M solution of an oxygen sensitive luminescent compound, tris(4,7-diphenyl 1,10-phenanthroline) ruthenium II chloride, in methanol. The solution is stirred for 6 hours at room temperature. The solution is then filtered, and the solvent allowed to evaporate in room air.

Preparation of a Hydrophilic, Photogelling, Cationic Matrix Polymer

To a round bottom flask is charged 100 ml. of a 1% (weight/volume) solution of poly(hydroxyethyl methacrylate) (molecular weight 1,000,000) in anhydrous pyridine. The pyridine solution is stirred, and to it is added 10 ml. of a 0.1% (weight/volume) solution of glycidyltrimethylammonium chloride. The solution is then warmed to 60° C. with mixing continued for a period of 24 hours. Following the 24 hour period, the solution is cooled to 0° C. in an ice bath, and 10 ml of a 0.1% (weight/volume) solution of acryloyl chloride in pyridine is slowly added. The resultant solution is stirred in the absence of all light for 2 hours. Following the reaction of the acryloyl chloride, the pyridine hydrochloride formed is filtered from the solution using a number 2 Whatman filter. The photogelling (i.e. crosslinking) polymer derivative is stored in a dark cool place prior to use.

Preparation of the Optrode 0.1 gram of the stained particles is dispersed in 50 ml. of the photogelling polymer derivative solution described above. To this solution is added 10 microliters of the photoinitiator 2,2-diethoxyacetophenone. A polymethyl methacrylate cored optical fiber is cleaved and/or polished to an optical grade finish. This fiber end is then dipped into the ion exchange resin/dye/polymer derivative solution and withdrawn. The fiber retains a small volume of the resin/dye/polymer solution. This small volume is purged of oxygen by placing the fiber tip in a stream of dry nitrogen for 5 minutes. The optrode is then formed by irradiating the tip with a high intensity blue light from a source such as an arc lamp. Alternatively, the light may be introduced to the end of the fiber by pumping with the arc lamp into the fiber end which was not dipped into the resin/dye/polymer. The formed optrode is then cleaned by soaking in distilled water for 24 hours.

How the Sensor Operates

The optics in this Example are the same as for Example 1, including the requirements of blue excitation (480 nm.). Upon excitation, the indicator emits a red 590 nm.) luminescent signal which is inversely proportional to the oxygen tension of the sample. Just as with Example 1, this emission signal is returned up the fiber, filtered, focused and detected.

EXAMPLE 3

A pH Fiber Optic Sensor

A pH sensor was prepared with a polyurethane urea matrix membrane. An aromatic polyether polyurethane urea (1 kg.) was synthesized by mixing together, at 95° C., 4,4-methylene bis-phenyl diisocyanate (220.3 grams and polytetramethylene glycol of molecular weight 650 (290 grams) in dimethyl acetamide (225 grams) for one hour. To this prepolymer was slowly added a solution of 1,4-butanediol (19.83 grams), water (3.97 grams), and dimethyl acetamide (225 grams). The polymerization was complete within two hours.

An adduct was formed of sulfurtrioxide and dimethyl acetamide in the following manner. Dimethyl acetamide (80 mls.) was placed in an Erlenmeyer flask containing a magnetic stirring rod. The flask was placed in an ice bath and mixed. Fuming sulfuric acid (20 mls.) containing from 20 to 30% sulfur trioxide was placed in a dropping funnel fitted to the Erlenmeyer flask. The sulfuric acid was dropped into the dimethyl acetamide solution at a sufficiently slow flow rate such that the exotherm from the complexation reaction did not exceed 80° C.

The polyurethane urea was then sulfonated. The urethane solution described above (100 grams) was heated to 70° to 80° C. and mixed. The sulfur trioxide dimethyl acetamide adduct (5 mls.) was added to the urethane and mixed for at least five minutes. The urethane was then precipitated from solution by pouring it into a blender containing water. The urethane was then washed repeatedly with distilled or slightly alkali water and vacuum dried. Successful sulfonation was confirmed by positive staining of the urethane with methylene blue dye.

A crosslinked polystyrene ion exchange resin containing quaternized ammonium groups was ground in a blender to particles less than 50 microns in size. The particles were sieved through a 500 mesh sieve, and only particles less than 30 microns in diameter were collected. These particles (50 grams) were mixed with phenol red dye (0.5 grams) in an aqueous solution buffered to pH 4. The solution was allowed to sit overnight at room temperature. The solution was then filtered through a number 2 Whatman filter, and the dyed particles were washed repeatedly with alternations of acid and alkali water. This washing was continued until no dye was observable in the eluent. The dyed particles were then collected and dried at 50° C. in a vacuum oven overnight.

The sulfonated polyurethane urea (2 grams) was dissolved in dimethyl acetamide (8 grams). Dyed particles (2 grams) were dispersed in this urethane solution. A polymethyl methacrylate core optical fiber, stripped of cladding to provide an optrode surface of about 0.5 cm. in length, was dipped into the urethane/dyed particle/dimethyl acetamide solution and slowly withdrawn. It was then dried at 60° C. and low humidity (less than 40% relative humidity). For the phenol red dye pH indicator of this Example, a light source was used having an absorbtion band centered around 558 nm. The light source interacts with the sensor material through an evanescent wave resulting from interference of the incident and reflected light. Because the light wave penetrates a portion of the sensing polymer, it is attenuated by the pH indicating dye retained by the ion exchange resin.

It will be understood that the embodiments of the present invention which have been described are illustrative of some of the applications of the principles of the present invention. Numerous modifications may be made by those skilled in the art without departing from the true spirit and scope of the invention as defined in the following claims.

We claim:

1. A fiber optic chemical sensor for monitoring at least one parameter of a fluid, comprising:
   an optical fiber waveguide having a distal end portion;
   a chemical sensor at said distal end portion said chemical sensor having an anionic hydrogel matrix membrane adhered to said distal end portion of the optical fiber waveguide;
   cationic ion exchange resin material dispersed within said anionic matrix membrane; and
   an anionic colorimetric indicator component electrostatically coupled to said cationic ion exchange resin material.

2. The chemical sensor according to claim 1, wherein said ion exchange resin material comprises ion exchange resin beads ground to resin powder.

3. The chemical sensor according to claim 1, wherein said ion exchange resin material is a powder of micron-sized ion exchange resin particles.

4. The chemical sensor according to claim 1, wherein said ion exchange resin material is water insoluble.

5. The chemical sensor according to claim 1, wherein said anionic colorimetric indicator component is irreversibly bound to said ion exchange resin material.

6. The chemical sensor according to claim 1, wherein said hydrogel matrix membrane is generally soluble in a solvent within which said ion exchange resin material is dispersible, and said hydrogel matrix membrane has a refractive index that allows the colorimetric indicator to be visible through said optical fiber waveguide.

7. The chemical sensor according to claim 1, wherein said hydrogel matrix membrane is a polyurethane urea having anionic moieties.

8. A fiber optic chemical sensor for monitoring at least one parameter of a fluid, comprising:
   an optical fiber waveguide having a distal end portion;

a chemical sensor at said distal end portion, said chemical sensor having a cationic hydrogel matrix membrane adhered to said distal end portion of the optical fiber waveguide;

anionic ion exchange resin material dispersed within said cationic matrix membrane; and a cationic indicator component electrostatically coupled to said anionic ion exchange resin material.

9. The chemical sensor according to claim 8, wherein said ion exchange resin material comprises ion exchange resin beads ground to resin powder.

10. The chemical sensor according to claim 8, wherein said ion exchange resin material is water insoluble.

11. The chemical sensor according to claim 8, wherein said anionic colorimetric indicator component is irreversibly bound to said ion exchange resin material.

12. The chemical sensor according to claim 8, wherein said cationic hydrogel matrix membrane is a hydrophilic photogelling matrix polymer.

13. A fiber optic chemical sensor for monitoring at least one parameter of a fluid, comprising:

an optical fiber waveguide having a distal end portion;

a chemical sensor at said distal end portion, said chemical sensor having a charged hydrogel matrix membrane adhered to said distal end portion of the optical fiber waveguide;

ion exchange resin material dispersed within said charged hydrogel matrix membrane, said ion exchange resin material having a charge opposite to that of said charged hydrogel matrix membrane; and a colorimetric indicator component electrostatically coupled to said ion exchange resin material, said colorimetric indicator component having the same charge as said charged hydrogel matrix material.

14. The chemical sensor according to claim 13, wherein said ion exchange resin material comprises ion exchange resin beads ground to resin powder.

15. The chemical sensor according to claim 13, wherein said ion exchange resin material is water insoluble.

16. The chemical sensor according to claim 13, wherein said anionic colorimetric indicator component is substantially irreversibly bound to said ion exchange resin material.

17. The chemical sensor according to claim 13, wherein said charged hydrogel matrix membrane is a hydrogel material selected from the group consisting of polyurethane ureas having charged moieties, copolymers of hydroxyalkyl methacrylates and tertiary aminoalkyl methacrylates, and copolymers of sulfoalkyl methacrylate salts and hydroxyalkyl methacrylate.

18. A process for making a fiber optic chemical sensor for monitoring at least one parameter of a fluid, comprising:

providing a charged ion exchange resin material in powdered form;

electrostatically coupling by mixing said powdered ion exchange resin material with a solution of a colorimetric indicator component having a charge opposite to the charge of the charged ion exchange resin powder in order to thereby form a stained ion exchange material which is said ion exchange resin powder electrostatically bound to said colorimetric indicator;

mixing a charged hydrogen component with said stained ion exchange material, said charged hydrogel component having a charge the same as that of said colorimetric indicator component and opposite to that of the ion exchange material in order to thereby provide an optrode composition of said stained ion exchange material dispersed in said charged hydrogel component; and affixing said optrode composition to a distal portion of an optical fiber waveguide.

19. The process according to claim 18, wherein said electrostatic coupling step includes placing said colorimetric indicator component into solution with said powdered ion exchange resin powder, and wherein said colorimetric indicator component is adsorbed into said ion exchange resin.

* * * * *

UNITED STATES PATENT AND TRADEMARK OFFICE
CERTIFICATE OF CORRECTION

PATENT NO. : 5,096,671

DATED : March 17, 1992

INVENTOR(S) : James A. Kane and Leonard Pinchuk

It is certified that error appears in the above-identified patent and that said Letters Patent is hereby corrected as shown below:

Col. 7, line 49, "charge" should read --charged--.

Signed and Sealed this

Fifth Day of October, 1993

Attest:

BRUCE LEHMAN

Attesting Officer

Commissioner of Patents and Trademarks